United States Patent
Quintana

[19]

[11] Patent Number: 5,992,249
[45] Date of Patent: Nov. 30, 1999

[54] TANTALUM LINED PROBE

[75] Inventor: Keith Quintana, Fairport, N.Y.

[73] Assignee: Pfaudler, Inc., Rochester, N.Y.

[21] Appl. No.: 08/797,752

[22] Filed: Feb. 7, 1997

[51] Int. Cl.[6] .................................................. G01D 21/00
[52] U.S. Cl. .......................................................... 73/866.5
[58] Field of Search ............................ 73/86, 866.5, 756,
73/863.81; 374/208; 324/689, 694, 698,
664; 204/404, 422, 423, 286

[56] References Cited

U.S. PATENT DOCUMENTS

| | | | |
|---|---|---|---|
| 3,772,178 | 11/1973 | Wilson | 204/286 |
| 4,200,834 | 4/1980 | Carter | 324/450 |
| 4,595,487 | 6/1986 | Nunlist | 204/433 |
| 4,617,511 | 10/1986 | Shaftel | 324/54 |
| 5,184,514 | 2/1993 | Cucci et al. | 73/706 |
| 5,230,248 | 7/1993 | Cucci et al. | 73/706 |
| 5,606,125 | 2/1997 | Lyons et al. | |

OTHER PUBLICATIONS

Data Sheet DS33–101–2, Fault Finder System 125, Pfaudler, Inc. Aug. 1991.

*Primary Examiner*—Robert Raevis
*Attorney, Agent, or Firm*—Michael L. Dunn

[57] ABSTRACT

An electronic probe assembly having a probe for introduction into a vessel, which vessel has a corrosion resistant liner. The assembly comprises a ring having a body wherein the body is defined by a circumferential exterior surface, an upper sealing surface, a lower sealing surface and a central surface defining a central hole. The body also has a probe access hole passing through the body from the exterior surface to the central hole. The upper surface, lower surface and defining surfaces of the central hole are covered by a contiguous layer of a corrosion resistant metal, which is preferably tantalum. A probe is mounted in the probe access hole such that an end of a sensor portion of the probe is integral with said lining over the central surface and such that the probe may be connected with an electrical conductor through the probe access hole. The end of the sensor preferably comprises platinum which is welded to the tantalum to become integral therewith. The assembly is readily mounted to a vessel at a flange surface by placing a first corrosion resistant gasket between the lower sealing surface and the flange surface and a second corrosion resistant gasket between the upper sealing surface and a cover and tightening the cover to the flange thus compressing and holding the gaskets and allowing access of the sensor to the interior of the vessel and otherwise electrically isolating said assembly from the interior of the vessel.

5 Claims, 3 Drawing Sheets

TANTALUM LINED PROBE

BACKGROUND OF THE INVENTION

This invention relates to probes or detectors for corrosion resistant vessels. Historically it has been difficult to provide access for detectors or probes into corrosion resistant vessels including tanks and conduits, especially when such vessels are lined with a contiguous, often brittle, material such as glass or ceramic. This is true for several reasons. It is difficult to provide small access holes through a glass or ceramic lining since such holes provide stress points which are often subject to failure. Furthermore, even after such an access hole is provided it is difficult to provide a reliable seal around the detector or probe which passes through the access hole. This is especially true since such seals are often required to be corrosion, pressure, heat and electrically resistant Such seals are usually made from a corrosion resistant thermoplastic material such as polytetrafluoroethylene, commonly sold under the trademark TEFLON. The reliability of the seal is therefore dependent upon the properties of the sealing material, the sealing surface and pressure applicable to the seal.

Numerous attempts have been made to overcome these problems but all of them require complex sealing mechanisms are unreliable or both. One such example is shown in U.S. Pat. No. 4,200,834, incorporated herein by reference. This patent illustrates problems associated with providing access to glass lined vessels by probes or detectors. In that patent the access is not only complex, but provides very little sealing surface area to prevent failure, e.g. gasket 31 or seal 19. Another complex construction is shown in U.S. Pat. No. 4,595,487, incorporated herein by reference. In that patent a small access hole is provided which is surrounded by a flange 15. The short bends around such a small hole result in stress points which subject a glass lining to failure. In addition sealing gasket 21 has very little sealing surface area which creates potential for gasket failure. U.S. Pat. No. 4,617,511, incorporated herein by reference, shows an electrode for introduction into a glass lined vessel. The assembly has a protruding electrode 1 sealed by means of a small gasket 7.

A unique and interesting approach to the problem is presented in Data Sheet DS33-101-2, Fault Finder System 125 of Pfaudler U.S., Inc., August 1991. The probe illustrated in FIG. 3 of that data sheet is essentially shown in FIG. 3 herein as prior art. This prior art probe has a ring having a glass coating 40 having sealing surfaces 44 for mating with flange surfaces of a vessel with intervening sealing gaskets. A probe 10 passes through the body to a central hole 18 of the ring. The probe is recessed to permit the area of a full circle within the central hole to permit full access through the central hole to a vessel. As a result surface area 44 has a restricted area 46 which is a weak area for holding a sealing gasket. In addition probe 10 is sealed within access hole 22 by means of Teflon ring seal 42. The probe relies upon this ring seal for both resistance to the contents and conditions within the vessel and electrical resistance to isolate the probe. The small nature of ring seal 42, the small sealing surface area and the difficulty of applying positive pressure to retain the ring seal, make the ring seal subject to more failures than are desirable.

BRIEF DESCRIPTION OF THE INVENTION

Figure 1:
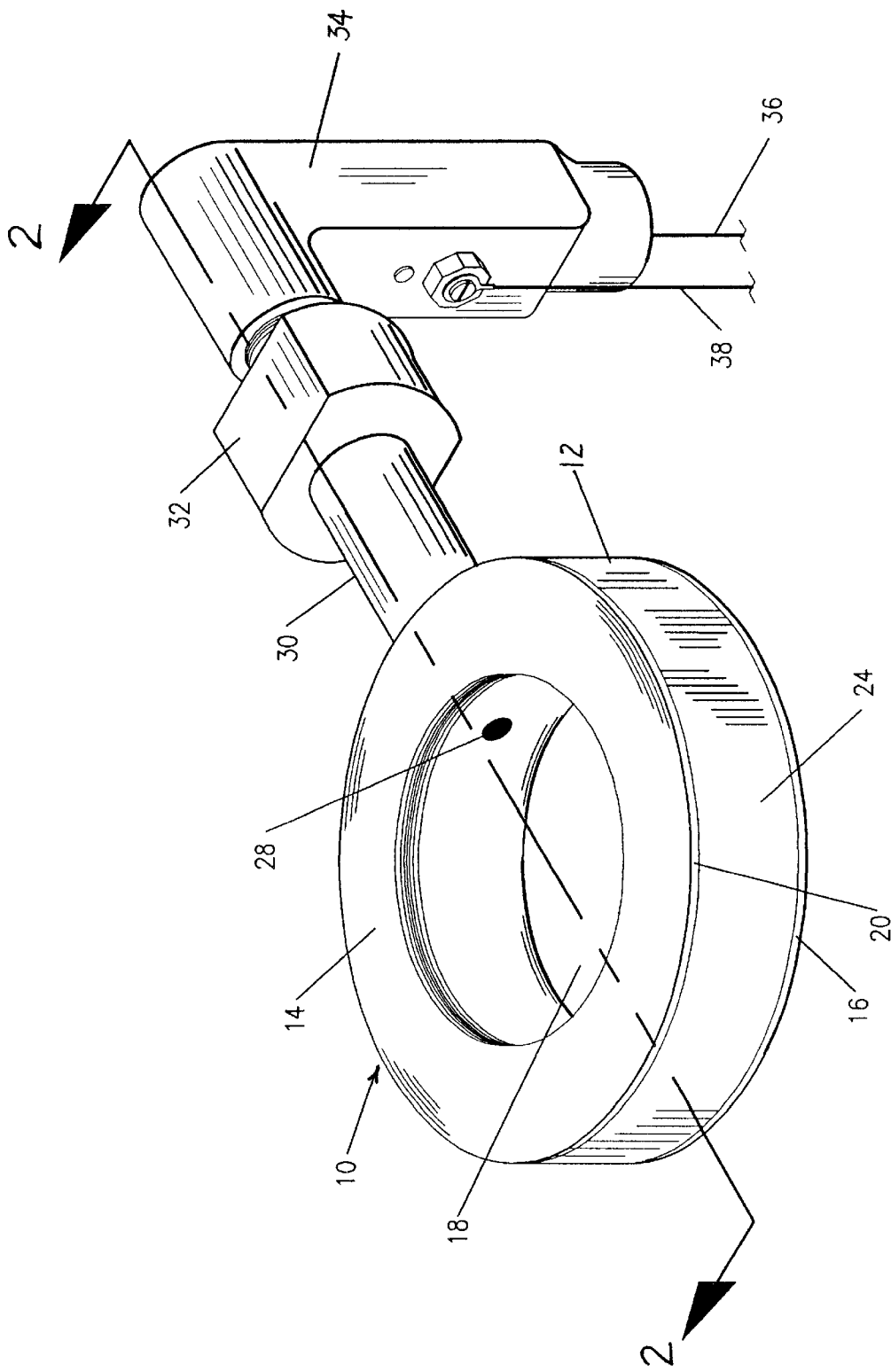
FIG. 1 shows a perspective view of an embodiment of a probe in accordance with the present invention.

The invention comprises an electronic probe assembly having a probe for introduction into a vessel, which vessel has a corrosion resistant liner. The assembly comprises a ring having a body wherein the body is defined by a circumferential exterior surface, an upper sealing surface, a lower sealing surface and a central surface defining a central hole. The body also has a probe access hole passing through the body from the exterior surface to the central hole.

The upper surface, lower surface and defining surfaces of the central hole are covered by a contiguous layer of a corrosion resistant metal, which is preferably tantalum.

A probe is mounted in the probe access hole such that an end of a sensor portion of the probe is integral with said lining over the central surface and such that the probe may be connected with a conductor through the probe access hole. The end of the sensor preferably comprises platinum which is welded to the tantalum to become integral therewith.

The assembly is readily mounted to a vessel at a flange surface by placing a first corrosion resistant gasket between the lower sealing surface and a first flange surface and a second corrosion resistant gasket between the upper sealing surface and a second flange surface and tightening the flange surfaces toward each other thus compressing and holding the gaskets and allowing access of the sensor to the interior of the vessel and otherwise electrically isolating said assembly from the interior of the vessel. At least one of the flange surfaces surrounds a hole into a vessel. The remaining flange surface may surround another hole into a vessel or may be a part of a cover.

The assembly may further include a coupling connected to the exterior surface at the location of the probe access hole. The coupling comprises an electrically resistant material and is hollow to permit passage of the electrical conductor connected with the probe.

DETAILED DESCRIPTION OF THE INVENTION

The electronic probe assembly of the invention is suitable for many purposes. For example, the probe may be used in a fault finder to detect leaks in a corrosion resistant layer by means of current flow which occurs between the probe and the leak. A number of such probes may be used in the same vessel and even stacked upon one another to provide a series of isolated sensors. Such an arrangement can be used to determine properties of vessel contents, e.g. electrical conductivity or pH.

Upper and lower sealing surfaces, as used herein, means upper and lower only as illustrated. It is to be understood that orientation may be varied without departing from the scope of the invention.

The body of the assembly may be made from any suitable material such as stainless or even mild steel; provided that the desired corrosion resistant layer can be applied thereto.

The invention may be more fully understood by reference to the preferred embodiment of the invention illustrated in the drawings.

Figure 2:
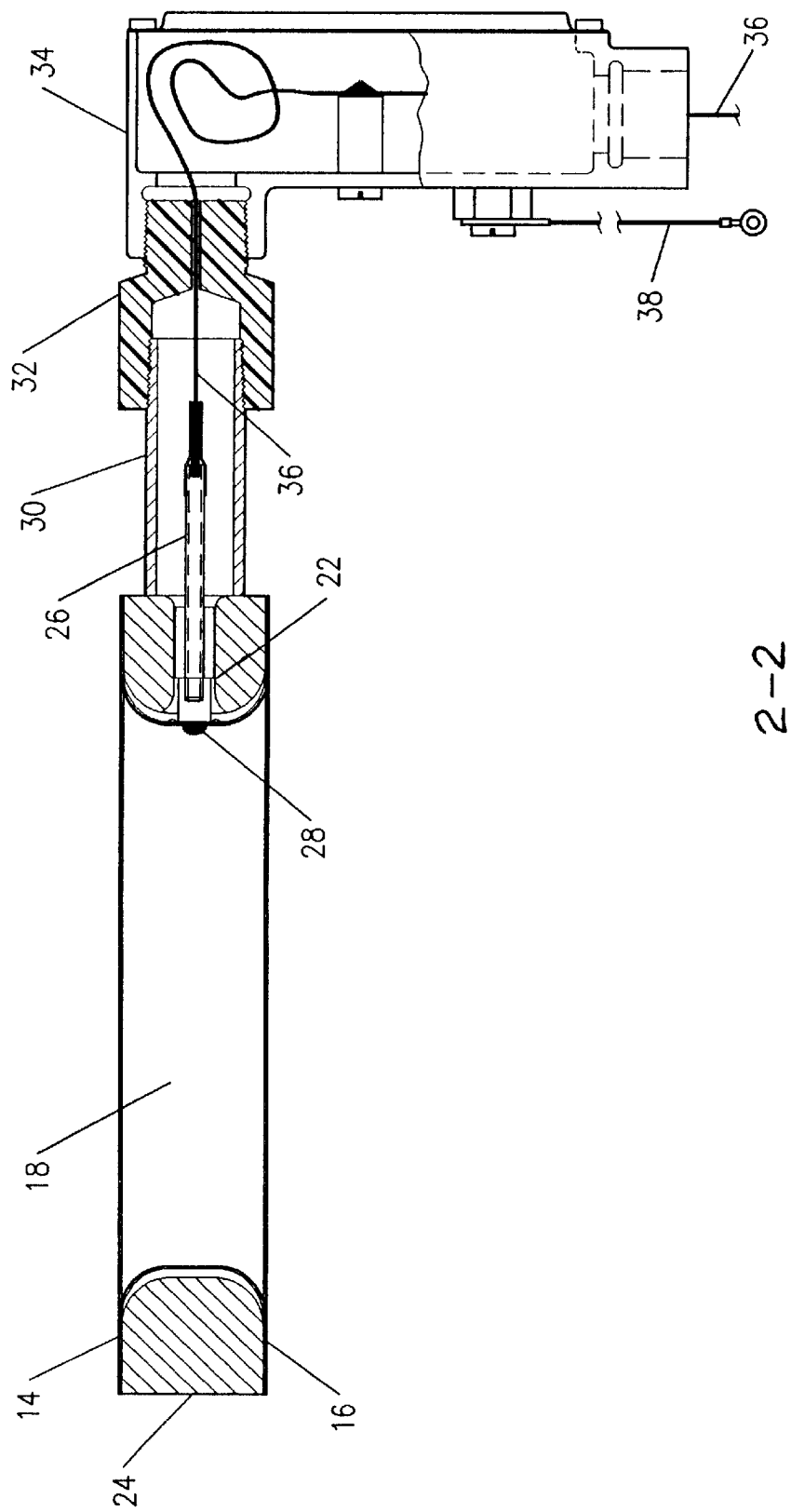
FIG. 2 shows a cross sectional view of the probe of FIG. 1 taken on line 2—2 of FIG. 1.
Figure 3:
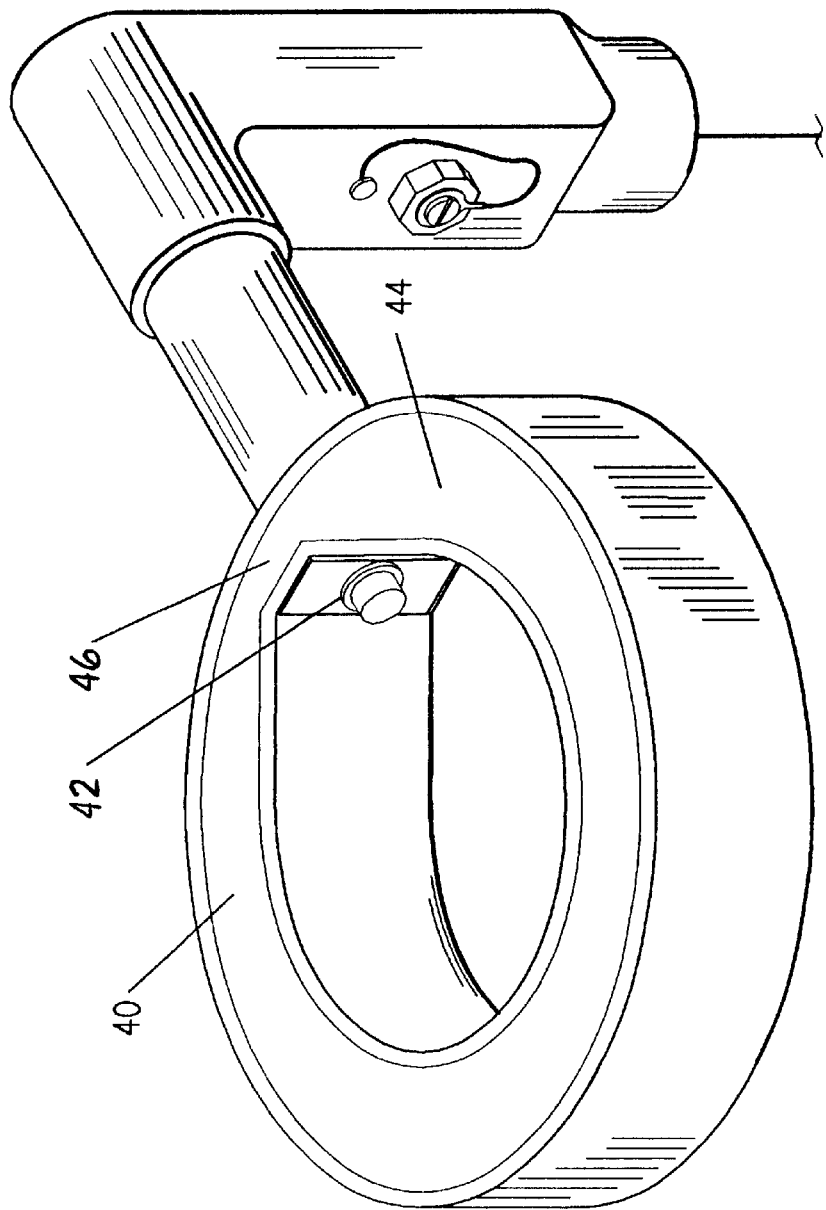
FIG. 3 illustrates a prior art probe.

As seen in FIGS. 1 and 2, a preferred embodiment of a probe assembly 10 comprises a ring having a body 12. The ring is defined by an upper sealing surface 14, a lower sealing surface 16, a circumferential exterior surface 24 and a central surface defining a central hole 18.

The upper surface, lower surface, and central surface are covered by contiguous layer 20 of a corrosion resistant metal.

The body 12, further has a probe access hole 22 passing through the body from exterior surface 24 to central hole 18.

A probe 26 is mounted in probe access hole 22 such that an end of a sensor portion 28 of the probe is integral with the corrosion resistant metal on the surface of central hole 18 and such that a portion of the probe exits from probe access hole 22 at exterior surface 24 so that the probe can be connected with electrical conductor 36.

A conduit 30 is attached to body 12 so that it surrounds access hole 22 and protects probe 26 and conductor 36. One end of an electrically non-conductive coupling is attached to conduit 30 to electrically isolate the probe and the other end of the coupling is connected to a junction box 34 grounded to a vessel (not shown) by means of ground wire 38. Conductor 36 passes through junction box 34 to electronic circuitry for analyzing signals from the probe.

When the assembly is mounted on a vessel, corrosion resistant and electrically resistant gaskets are placed upon surfaces 16 and 14 and sandwiched between flanges. In that way the entire assembly is electrically isolated and large sealing surfaces are employed which are more resistant to harsh corrosion, pressure and temperature conditions.

What is claimed is:

1. An electronic probe assembly having a probe for introduction into a vessel, which vessel has a corrosion resistant liner, said assembly comprising a ring having a body, said body being defined by a circumferential exterior surface, an upper sealing surface, a lower sealing surface and a central surface defining a central hole;

said upper surface, said lower surface and defining surfaces of the central hole being covered by a contiguous layer of a corrosion resistant metal; said body further having a probe access hole passing through the body from the exterior surface to the central hole;

a probe mounted in the probe access hole such that an end of a sensor portion of the probe is in contact with said corrosion resistant metal of the central surface and such that the probe may be connected with an electrical conductor through the probe access hole;

said assembly being readily mounted to a vessel at a flange surface thereof by placing a first corrosion resistant gasket between the lower sealing surface and a first flange surface and a second corrosion resistant gasket between the upper sealing surface and a second flange surface and tightening the flange surfaces toward each other thus compressing and holding the gaskets and allowing access of the sensor to communicate with the vessel and otherwise electrically isolating said assembly from the interior of the vessel.

2. The assembly of claim 1 wherein the sensor end is platinum.

3. The assembly of claim 1 further including a coupling connected to the exterior surface at the location of the probe access hole said coupling comprising an electrically resistant material and being hollow to permit passage of the electrical conductor connected with the probe.

4. An electronic probe assembly having a probe for introduction into a vessel, which vessel has a corrosion resistant liner, said assembly comprising a ring having a body, said body being defined by a circumferential exterior surface, an upper sealing surface, a lower sealing surface and a central surface defining a central hole;

said upper surface, said lower surface and defining surfaces of the central hole being covered by a contiguous layer of tantalum corrosion resistant metal; said body further having a probe access hole passing through the body from the exterior surface to the central hole;

a probe mounted in the probe access hole such that an end of a sensor portion of the probe is platinum and is welded to said corrosion resistant metal of the central surface and such that the probe may be connected with an electrical conductor through the probe access hole;

said assembly being readily mounted to a vessel at a flange surface thereof by placing a first corrosion resistant gasket between the lower sealing surface and a first flange surface and a second corrosion resistant gasket between the upper sealing surface and a second flange surface and tightening the flange surfaces toward each other thus compressing and holding the gaskets and allowing access of the sensor to communicate with the vessel and otherwise electrically isolating said assembly from the interior of the vessel.

5. An electronic probe assembly having a probe for introduction into a vessel, which vessel has a corrosion resistant liner, said assembly comprising a ring having a body, said body being defined by a circumferential exterior surface, an upper sealing surface, a lower sealing surface and a central surface defining a central hole;

said upper surface, said lower surface and defining surfaces of the central hole being covered by a contiguous layer of a corrosion resistant metal; said body further having a probe access hole passing through the body from the exterior surface to the central hole;

a probe mounted in the probe access hole such that an end of a sensor portion of the probe is integral with said corrosion resistant metal of the central surface and such that the probe may be connected with an electrical conductor through the probe access hole;

said assembly being readily mounted to a vessel at a flange surface thereof by placing a first corrosion resistant gasket between the lower sealing surface and a first flange surface and a second corrosion resistant gasket between the upper sealing surface and a second flange surface and tightening the flange surfaces toward each other thus compressing and holding the gaskets and allowing access of the sensor to communicate with the vessel and otherwise electrically isolating said assembly from the interior of the vessel;

wherein the corrosion resistant metal is tantalum; and wherein the sensor end is platinum and is welded to the tantalum to become integral therewith.

* * * * *